(12) United States Patent
Ackerman et al.

(10) Patent No.: US 6,802,825 B2
(45) Date of Patent: Oct. 12, 2004

(54) ACCESS CATHETER APPARATUS FOR USE IN MINIMALLY INVASIVE SURGERY AND DIAGNOSTIC PROCEDURES IN THE UTERUS AND FALLOPIAN TUBES

(75) Inventors: Bernard Ackerman, Metuchen, NJ (US); Robert M. Landis, Mountainside, NJ (US)

(73) Assignee: CooperSurgical, Inc., Trumbull, CT (US)

( * ) Notice: Subject to any disclaimer, the term of this patent is extended or adjusted under 35 U.S.C. 154(b) by 349 days.

(21) Appl. No.: 09/898,148

(22) Filed: Jul. 3, 2001

(65) Prior Publication Data

US 2003/0009128 A1 Jan. 9, 2003

(51) Int. Cl.$^7$ ................................................ A61M 5/32
(52) U.S. Cl. ........................ 604/174; 604/523; 604/528; 604/537; 604/915; 604/103.03; 606/193
(58) Field of Search ................................ 604/174, 178, 604/514, 515, 517, 104, 96.01, 103.03, 103.07, 167.06, 170.01, 170.02, 167.01, 264, 523, 528, 533, 537, 284, 915, 916, 920, 912; 606/193–195, 158

(56) References Cited

U.S. PATENT DOCUMENTS

| | | | | |
|---|---|---|---|---|
| 4,777,951 A | * | 10/1988 | Cribier et al. | ............... 606/194 |
| 4,994,032 A | * | 2/1991 | Sugiyama et al. | ...... 604/103.09 |
| 5,104,377 A | * | 4/1992 | Levine | ................... 604/101.05 |
| 5,372,584 A | | 12/1994 | Zink et al. | |
| 5,389,089 A | | 2/1995 | Bauer et al. | |
| 5,476,450 A | * | 12/1995 | Ruggio | ......................... 604/28 |
| 5,624,399 A | * | 4/1997 | Ackerman | ............. 604/103.03 |
| 5,693,015 A | * | 12/1997 | Walker et al. | ........... 604/96.01 |
| 5,730,734 A | * | 3/1998 | Adams et al. | .............. 604/533 |
| 5,807,330 A | * | 9/1998 | Teitelbaum | .............. 604/96.01 |
| 5,935,098 A | | 8/1999 | Blaisdell et al. | |

* cited by examiner

Primary Examiner—Brian L. Casler
Assistant Examiner—Cris L. Rodriguez
(74) Attorney, Agent, or Firm—Lathrop & Gage LC

(57) ABSTRACT

A catheter apparatus for gaining access into the uterine cavity in order to perform minimally invasive surgery or diagnostic procedures related to a uterus and fallopian tubes, includes a single-lumen catheter; and an elongated balloon disposed distally on the single-lumen catheter for insertion into a cervical canal of the uterus. The balloon has opposing portions which occlude openings of the cervical canal when inflated. A fluid displacement sleeve is slidably disposed over the single-lumen catheter. The sleeve is moveable over the elongated balloon to inflate the portions of the balloon which are adjacent the opposite openings of the cervical canal when the balloon is inserted therein. Because there is no need for a balloon inflation lumen, the outer diameter of the catheter can be minimized and the cost of the apparatus is reduced.

8 Claims, 5 Drawing Sheets

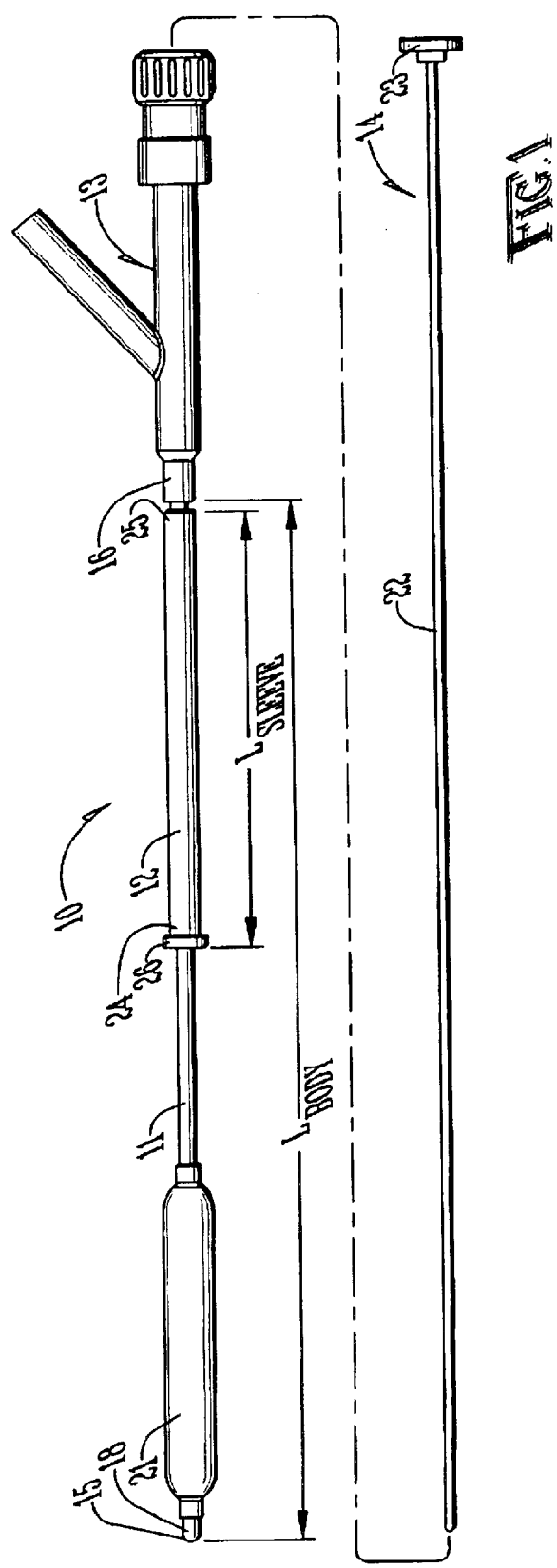

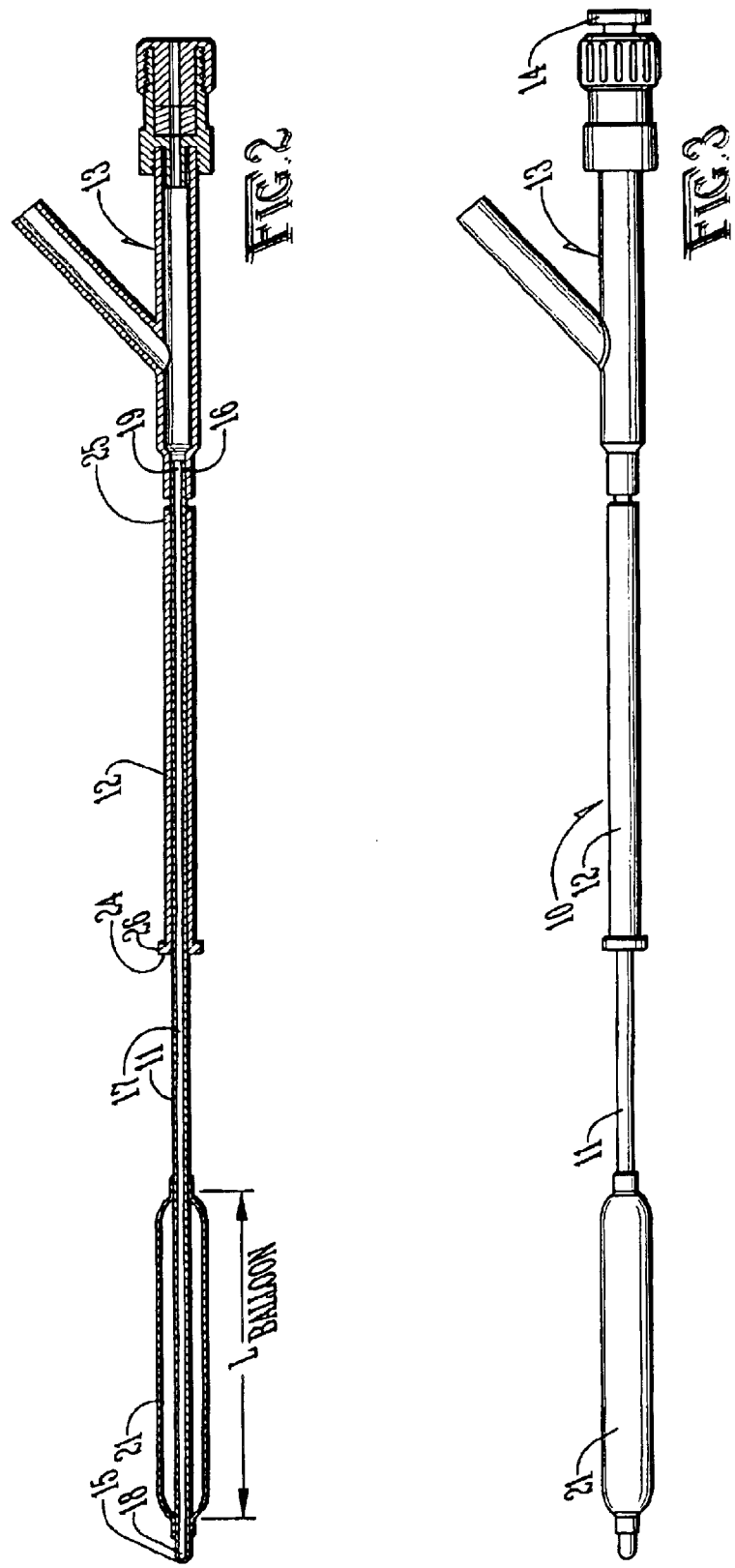

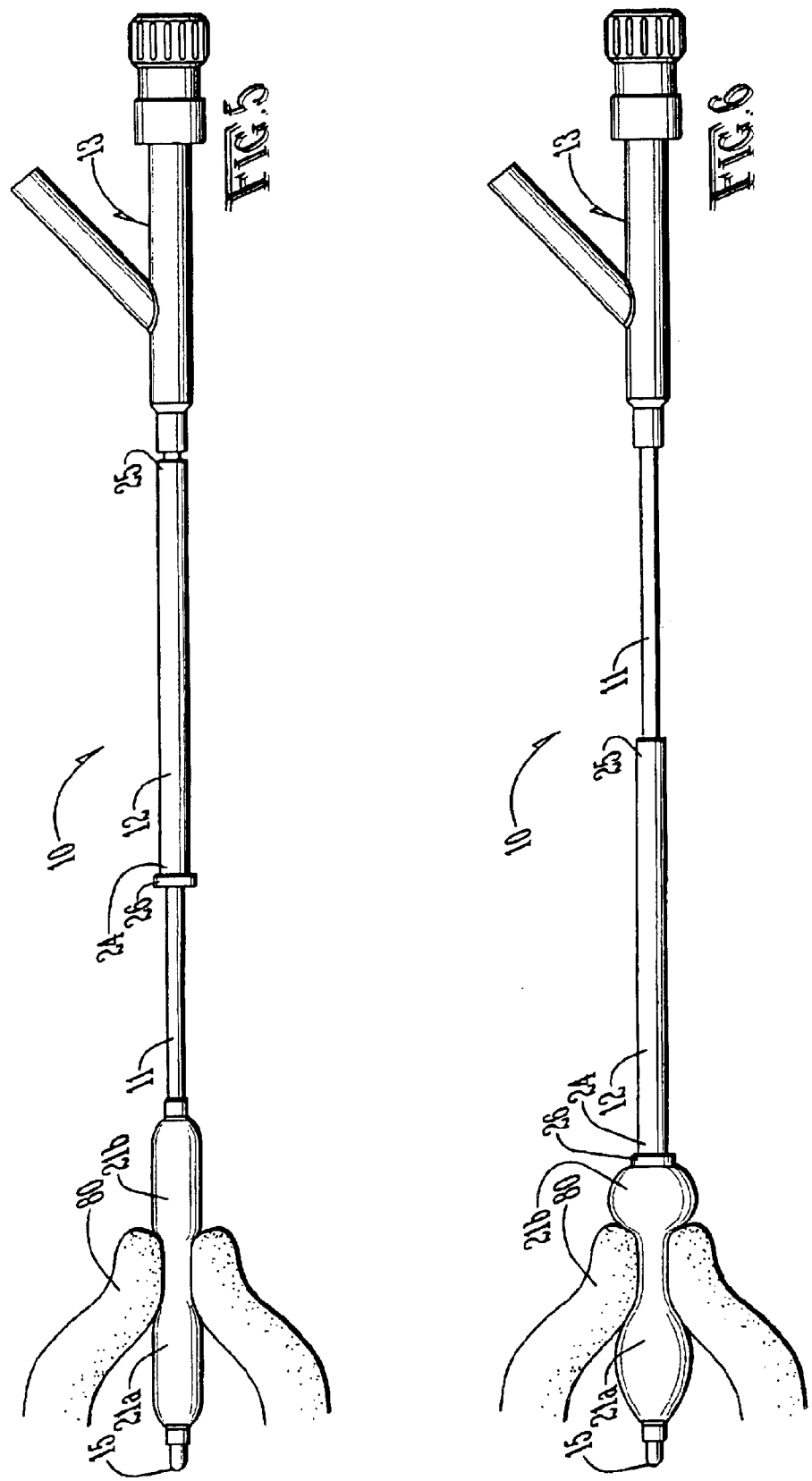

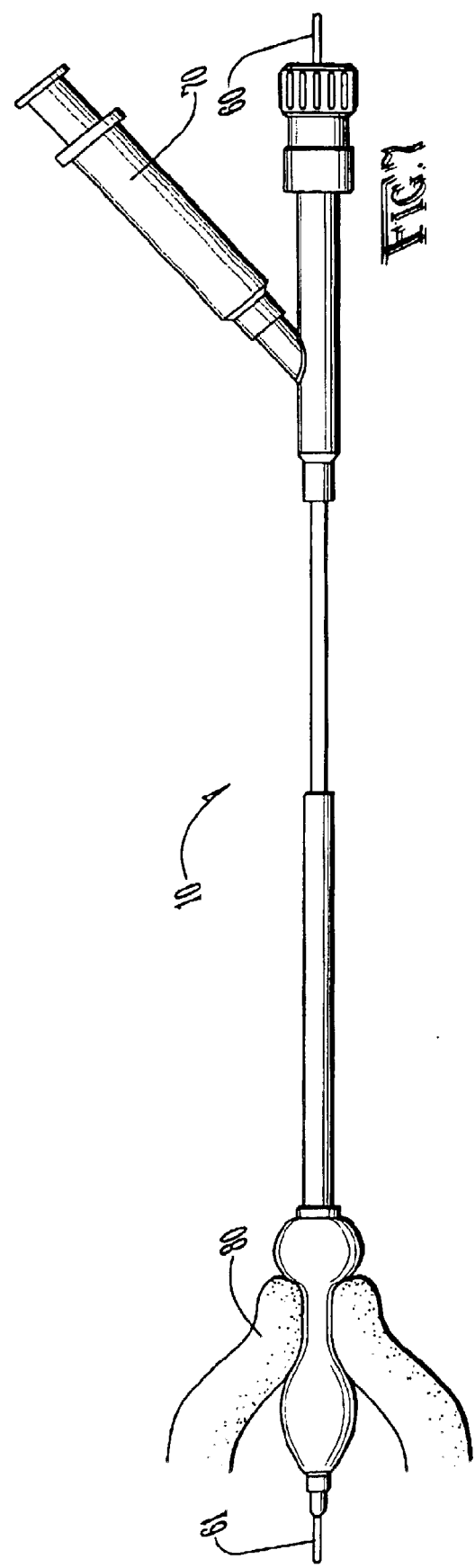

ACCESS CATHETER APPARATUS FOR USE IN MINIMALLY INVASIVE SURGERY AND DIAGNOSTIC PROCEDURES IN THE UTERUS AND FALLOPIAN TUBES

RELATED APPLICATIONS

The present document contains material related to the material of copending, U.S. patent application Ser. No. 09/782,859, entitled, "Cervical Occluding Double Balloon Catheter", filed Feb. 14, 2001 now U.S. Pat. No. 6,511,469 and U.S. patent application Ser. No. 09/808,080, entitled "Esophageal Balloon Catheter Device", filed Mar. 14, 2001.

FIELD OF THE INVENTION

The present invention relates to a catheter apparatus and more particularly, to an access catheter apparatus that enables minimally invasive surgery to be performed in the uterus or selective examination of the fallopian tubes.

BACKGROUND OF THE INVENTION

Access catheters can be used in non-surgical diagnostic procedures that enable the examination of the uterus and fallopian tubes. One such procedure known as hysterosonography, employs contrast agents and ultrasound imaging techniques for viewing the anatomical structures of the uterus. In hysterosonography, a fine flexible catheter equipped with an inflatable balloon is used to gain access into the uterus. This is accomplished by inserting the catheter into the cervical canal or the uterus and inflating the balloon with saline to block the cervical canal. A contrast agent, such as saline, is then injected through the catheter to fill the uterus so that it can be viewed using ultrasound imaging techniques.

It may also be desirable to use an access catheter to gain access into the uterus for the purpose of carrying out a minimally invasive surgical procedure, such as a biopsy. In such a procedure, the access catheter is inserted through the cervix into the uterus. A contrast agent, such as saline or water, is injected through the catheter to fill the uterus so that any suspected pathology can be viewed using ultrasound imaging techniques. A surgical instrument, such as a biopsy needle or snare, is then passed through the catheter and into the uterus and manipulated to perform the surgery.

Another desirable use for an access catheter is as a conduit for a smaller diameter catheter used for selective examination of fallopian tubes. Such a catheter is passed through the access catheter and manipulated into the entrance of either fallopian tube. Contrast medium is then injected through the inner catheter to determine the degree of patency of the tube. In this application, X-ray techniques can be used as well as ultrasound procedures.

Access catheters that are suitable for performing minimally invasive surgery in the uterus or selective examination of the fallopian tubes must be stable when positioned in the cervical canal. Previous guided access catheter designs typically employ two inflatable, distally located balloons for stabilizing the catheter. Such catheters are constructed with multiple lumens, two for inflating the balloons, one for inserting the surgical instrument, and one for injecting the contrast agent. These multi-lumen catheter designs necessarily have relatively large outer diameters, which typically measure about 4 mm (12 french). The relatively large outer diameters of these prior catheter designs can cause patient discomfort and or trauma. Moreover, these designs are relatively complex, thus increasing the cost of the device.

Accordingly, an access catheter apparatus for performing minimally invasive surgery in the uterus or selective examination of the fallopian tubes is needed that overcomes the problems associated with previous access catheter designs.

SUMMARY OF THE INVENTION

The invention is directed to a catheter apparatus for gaining access into the uterine cavity in order to perform minimally invasive surgery in a uterus or selective examination of the fallopian tubes. The catheter apparatus comprises a single-lumen tubular body, and an elongated balloon disposed distally on the tubular body for insertion into a cervical canal of the uterus. The balloon is affixed to the tubular body and sealed with a fixed residual volume of fluid. The balloon includes opposing portions that occlude openings of the cervical canal when fluid displacement in one portion of the balloon causes other portions of the balloon to inflate.

One aspect of the catheter apparatus involves a fluid displacement sleeve, which is slidably disposed over the single-lumen tubular body. The sleeve is moveable over the elongated balloon to displace fluid in the proximal portion of the balloon thereby inflating the portions of the balloon which are adjacent the opposite openings of the cervical canal when the balloon is inserted therein.

In another aspect of the catheter apparatus, the inflated portions of the balloon define a barbell-shape balloon structure when the balloon is inflated in the cervical canal.

In a further aspect of the catheter apparatus, a surgical instrument insertion adapter assembly is disposed at a proximal end of the single-lumen tubular body.

In still a further aspect of the catheter apparatus, a removable stylet is optionally provided for stiffening the single-lumen tubular body to facilitate insertion thereof in the cervical canal.

BRIEF DESCRIPTION OF THE DRAWINGS

The advantages, nature, and various additional features of the invention will appear more fully upon consideration of the illustrative embodiments now to be described in detail in connection with accompanying drawings wherein:

FIG. 1 is an elevational view of an access catheter apparatus according to an embodiment of the invention;

FIG. 2 is a sectional view of the catheter body of the apparatus of FIG. 1;

FIG. 3 is an elevational view of the access catheter apparatus with the removable stylet assembly inserted through the catheter body;

FIG. 5 is a diagrammatic view of the catheter apparatus inserted into the cervical canal of a subject uterus prior to inflation of the balloon portions;

FIG. 6 is a diagrammatic view of the catheter apparatus inserted into the cervical canal of a subject uterus after inflation of the balloon portions; and FIG. 7 is a diagrammatic view of the catheter apparatus inserted into the cervical canal of a subject uterus after attachment of the removable surgical instrument insertion adapter assembly to the catheter body. This view shows how the catheter apparatus is used for gaining access into the uterine cavity in order to perform minimally invasive surgery in a uterus and its associated fallopian with a surgical instrument.

Figure 4A:
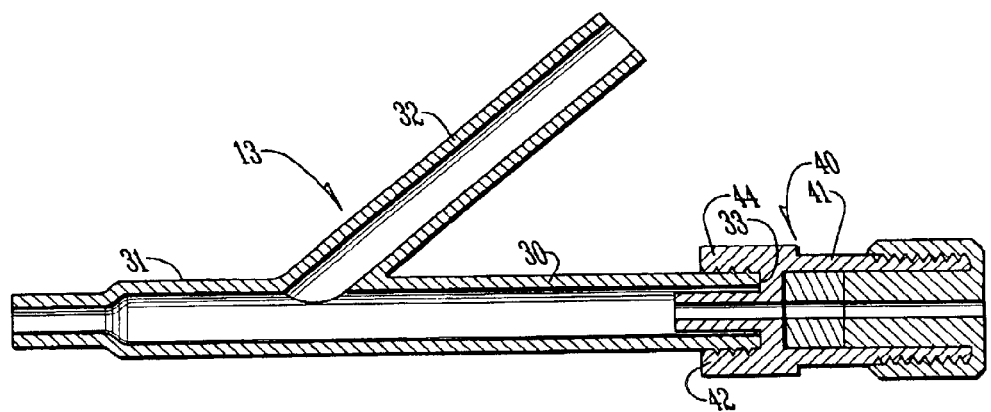
FIG. 4A is a sectional view of the removable surgical instrument insertion adapter assembly.

It should be understood that the drawings are for purposes of illustrating the concepts of the invention and are not necessarily to scale.

DETAILED DESCRIPTION OF THE INVENTION

Referring to the drawings wherein like reference numerals identify similar or like elements throughout the several views, and initially to FIG. 1, there is shown an access catheter apparatus 10 according to an exemplary embodiment of the invention. The catheter apparatus 10 generally comprises a flexible tubular catheter body 11, a semi-rigid fluid displacement sleeve 12, a surgical instrument insertion adapter assembly 13, and optionally, a removable stylet assembly 14.

As collectively shown in FIGS. 1 and 2, the tubular catheter body 11 includes a distal end 15 and a proximal end 16. ("Distal end" refers to the end furthest from the person holding the apparatus, and "proximal end" refers to the end closest to the holder of the apparatus.) An elongated inflatable balloon 21 (shown in the deflated state), about 4 inches in length $L_{balloon}$, is sealingly affixed to and encloses a distal portion of the catheter body 11. The balloon 21 may be made from an elastomeric material such as polyurethane, poly(vinyl chloride) or any other suitable material. The balloon 21 is sealed with a fixed residual volume of fluid, e.g., air and/or saline solution. The elongated construction of the balloon 21 enables it to be positioned in the cervical canal such that distal and proximal end portions 21a, 21b of the balloon 21 extend past the openings of the canal (FIGS. 5–7). The distal and proximal portions 21a, 21b of the balloon 21 are inflated and deflated by the operation of the fluid displacement sleeve 12 as will described further on. When inflated, the two balloon portions 21a, 21b permit stable positioning of the catheter body 11 in the cervical canal. The portion of the balloon connecting the two portions 21a, 21b, which resides in the cervical canal, inflates slightly within the canal, as it is restricted by cervical tissue.

The catheter body 11 includes a single lumen 17 that extends the entire length $L_{body}$ thereof and communicates with the external environment via distal opening 18 and proximal opening 19 at the distal and proximal ends 15, 16 of the body 11. The lumen 17 provides a fluid communication path for injecting a diagnostic fluid, such as saline or a contrast medium, into the uterine cavity and provides a means for accessing the uterine cavity with a surgical instrument to perform a surgical procedure, or accessing the uterine cavity with other type of devices, such as diagnostic instruments. Fluid injection is completely independent of the mechanism of balloon inflation. By way of example and not limitation, the lumen 17 may have an inner diameter of approximately 1.9 mm. Such an inner diameter enables, for example, a surgical instrument with a maximum outer diameter of up to about 1.66 mm (5 french) to be slidably inserted through the lumen 17 and into the uterine cavity. The surgical instrument insertion adapter assembly 13 is integrally attached at the proximal end 16 of the catheter body 11. Alternatively, the surgical instrument insertion adapter assembly 13 may be attached at the proximal end 16 of the catheter body 11 using a Luer lock arrangement. The catheter body 11 may be made from an opaque or clear flexible material such as polyurethane or any other suitable material.

As one of ordinary skill in the art will appreciate, no additional lumens are required within the catheter body 11 of the present invention to inflate or deflate the balloon 21 because the balloon 21 sealingly contains the fixed residual volume of fluid, which is displaced by operation of the fluid displacement sleeve 12 to inflate or deflate the balloon 21. This feature advantageously permits the outside diameter of the catheter body 11 to be reduced. The catheter body 11 has an outer diameter, which is typically only about 2.3 mm (7 french). This is in contrast to conventional multi-lumen catheter designs which have relatively large outer diameters, that typically measure about 4 mm (12 french). The slimmer catheter body 11 of the present invention will provide a beneficial reduction in patient discomfort and or trauma. Moreover, the less complex single lumen design of the catheter body 11 decreases the cost of the catheter apparatus 10, hence, reducing the cost of the surgical procedure.

Although the outer diameter of the catheter body 11 is typically about 2.3 mm in other embodiments of the invention, the outer diameter may be smaller or larger. The specific dimension of the outer diameter of the catheter body 11 depends mainly upon the diametrical dimensions of the instrument intended to be inserted through the catheter apparatus.

As shown in FIG. 1, the optional stylet assembly 14 of the catheter apparatus 10 typically comprises a wire 22 (stylet), the proximal end of which is permanently affixed to a central portion of a holder 23. The stylet 22 extends through the lumen 17 of the catheter body 11 from the proximal end 16 thereof to a point approximately adjacent a point 1 to 2 cm from the distal end thereof, when inserted in the catheter body 11. The stylet 22 is slidably threaded into the lumen 17 of the catheter body 11 as shown in FIG. 3. The stylet assembly 14 may be employed to prevent the catheter apparatus 10 from bending and flexing excessively in the vagina, in cases where insertion of the catheter apparatus 10 into the cervical canal is difficult. Once the catheter apparatus 10 has been inserted into the cervical canal, the stylet assembly 14 can then be removed.

Referring again to FIGS. 1 and 2, the fluid displacement sleeve 12 of the catheter apparatus 10 has a distal end 24 and a proximal end 25. The fluid displacement sleeve 12 may be made from any suitable semi-rigid material such as polypropylene. The distal end 24 of the sleeve 12 terminates with an outwardly extending rim 26. The fluid displacement sleeve 12 has a length $L_{sleeve}$ which may be about 40% percent of the length $L_{body}$ of the catheter body 11. This enables the fluid displacement sleeve 12 to be slidably moved along the catheter body 11 in both the distal and proximal directions to inflate and deflate the elongated balloon 21.

Referring now to FIG. 4A, the surgical instrument insertion adapter assembly 13 includes a Y-shape tubing member 30 having main leg 31 and an angled side port 32. The angled side port 32 extends back toward a proximal end 33 of the main leg 31 and is adapted for removably coupling a syringe (FIG. 7).

Figure 4B:
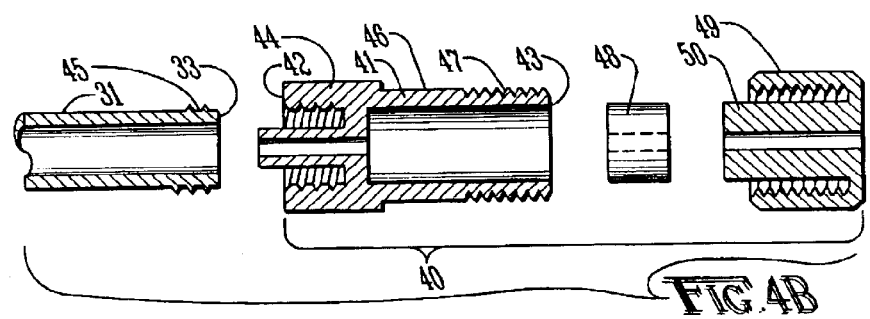
FIG. 4B is an exploded sectional view of the removable surgical instrument insertion adapter assembly of FIG. 4A.

As best seen in FIG. 4B, the proximal end 33 of the main leg 31 may be adapted for threadedly receiving a conventional Touhy Borst assembly 40 by configuring the proximal end 33 of the main leg 31 as a conventional female Luer hub. The Touhy Borst assembly 40 typically includes a cylindrical body 41 with distal and proximal ends 42, 43. The distal end 42 includes a male Luer hub 44 that mates with a female Luer hub 45 formed by the proximal end 33 of the main leg 31. The outer surface 46 of the cylindrical body 41 at the proximal end 43 thereof includes a thread arrangement 47.

An elastomeric bushing 48 is disposed within the cylindrical body 41 between the hub 44 and a cap member 49. The cap member 49 includes a tubular plug element 50 that compresses the bushing 48 against the hub 44 when the cap member 49 is screwed down onto the cylindrical body 41, thereby reducing the inner diameter of the bushing 48.

Figure 4C:
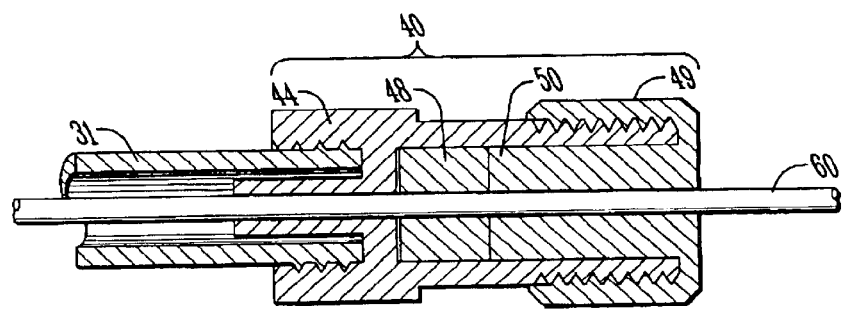
FIG. 4C is a sectional view of the removable surgical instrument insertion adapter assembly with a surgical instrument inserted therethrough.

As shown in FIG. 4C, when a surgical instrument 60 is inserted through the Touhy Borst assembly 40 and the cap member 49 is screwed down sufficiently tight, the bushing 48 creates a substantially fluid tight seal around the surgical instrument 60, thereby preventing excessive fluid leakage out the cap member 49 while still allowing the surgical instrument 60 to be manipulated within the catheter apparatus by rotating it, pushing it in, and pulling it out. The Touhy Borst assembly 40 may also be used to create a substantially fluid tight seal around the stylet 22 of the stylet assembly 14, when the stylet assembly 14 is used.

Referring to FIG. 5, the catheter apparatus 10 may be operated by positioning the fluid displacement sleeve 12 proximally on the catheter body 11, introducing the catheter apparatus 10 into the vaginal canal and inserting the distal end 15 of the catheter body 11 through the cervical canal so that the distal and proximal portions 21a, 21b of the balloon are positioned adjacent the exterior and interior OS of the cervical canal. If necessary or desired, the stylet assembly 14 (not shown) can be used to stiffen the catheter body 11 to aid in the insertion of the catheter body 11 into the cervical canal. The stylet assembly 14 may be assembled to the catheter body 11 by inserting the distal end of the stylet 22 into and through the surgical instrument insertion adapter assembly 13 and threading the stylet 22 through the lumen 17 of the catheter body 11 via the opening 19 at the proximal end 16 thereof.

As shown in FIG. 6, the distal and proximal portions 21a, 21b of the balloon 21 are inflated by sliding the fluid displacement sleeve 12 distally along the catheter body 11 so that the sleeve 12 slides over the end of the proximal portion 21b of the balloon 21. As the sleeve slides over the proximal portion 21b of the balloon 21, the fixed volume of fluid (e.g. air or saline) sealingly contained therein is displaced or redistributed to inflate and expand the distal and proximal portions 21a, 21b of the balloon 21, thereby forming a barbell-shape balloon structure which conforms to and thus occludes the exterior and interior OS of the cervical canal and sealingly affixes and stabilizes the catheter apparatus 10 in place therein. If used, the stylet assembly 14 can now be removed from the catheter body 11.

As shown in FIG. 7, an echogenic surgical instrument 60, such as a biopsy needle or snare, is then threaded through the Touhy Borst assembly 40, the main leg 31 of the tubing member 30, and the lumen 17 (not visible) of the catheter body 11. The cap 49 of the Touhy Borst assembly 40 is then tightened sufficiently to create a fluid seal around the instrument 60 but still allowing in-and-out, and rotational movement of the instrument 60, and a syringe 70 filled with a contrast medium is coupled to the side port 32 of the adapter assembly 13. The contrast medium in the syringe 70 is injected into the uterine cavity of the uterus to enable imaging of the uterus and the distal end 61 of the surgical instrument 60 during the surgical procedure.

When it is desirable to deflate the portions of the balloon 21, the fluid displacement sleeve 12 is moved proximally along the catheter body 11. This allows the fluid in the distal and proximal balloon portions 21a, 21b to redistribute throughout the entire interior of the balloon 21 so that the catheter apparatus 10 can be withdrawn through the cervix 80.

Although the access catheter apparatus 10 has been described for surgical diagnostic entry into the uterine cavity, one of ordinary skill in the art will recognize its usefulness in other related procedures.

Further, while the foregoing invention has been described with reference to the above embodiments, various modifications and changes can be made without departing from the spirit of the invention. Accordingly, all such modifications and changes are considered to be within the scope of the appended claims.

What is claimed is:

1. A catheter apparatus for gaining access into the uterine cavity in order to perform minimally invasive surgery or diagnosis in a uterus and its associated fallopian tubes, the catheter apparatus comprising:
   a single-lumen catheter;
   an elongated balloon disposed distally on the single-lumen catheter for insertion into a cervical canal of the uterus, the balloon sealed containing a fixed internal residual volume of fluid;
   a fluid displacement sleeve slidably disposed over the single-lumen catheter, the sleeve being moveable over the elongated balloon to displace the fluid from a proximal portion of the balloon to opposing portions of the balloon which are adjacent the opposite openings of the cervical canal when the balloon is inserted therein, to inflate the opposing portions of the balloon; and
   a surgical instrument insertion adapter assembly disposed at a proximal end of the single-lumen catheter.

2. The catheter apparatus according to claim 1, wherein the single-lumen catheter is flexible.

3. The catheter apparatus according to claim 1, further comprising a removable stylet for stiffening the single-lumen catheter to facilitate insertion thereof in the cervical canal.

4. The catheter apparatus according to claim 1, wherein the fluid displacement sleeve is semi-rigid.

5. The catheter apparatus according to claim 1, wherein the inflated portions of the balloon define a barbell-shape balloon structure when inflated in the cervical canal.

6. The catheter apparatus according to claim 1, wherein the surgical instrument insertion adapter assembly includes a compressible sealing element for creating a substantial fluid tight seal around a surgical instrument.

7. The catheter apparatus according to claim 6, wherein the surgical instrument insertion adapter assembly includes a port for introducing a contrast medium into the uterine cavity via the single-lumen catheter.

8. The catheter apparatus according to claim 1, wherein the surgical instrument insertion adapter assembly includes a port for introducing a contrast medium into the uterine cavity via the single-lumen catheter.

* * * * *